United States Patent [19]

Choe

[11] Patent Number: 4,703,096

[45] Date of Patent: Oct. 27, 1987

[54] NOVEL DIACETYLENIC AND POLYDIACETYLENIC COMPOSITIONS

[75] Inventor: Eui W. Choe, Randolph, N.J.

[73] Assignee: Celanese Corporation, New York, N.Y.

[21] Appl. No.: 854,273

[22] Filed: Apr. 21, 1986

[51] Int. Cl.[4] ............................................. C08F 26/00
[52] U.S. Cl. .................................. 526/248; 564/305; 558/418; 526/285
[58] Field of Search ................ 526/248, 285; 564/305; 558/418

*Primary Examiner*—Paul R. Michl
*Assistant Examiner*—Alex H. Walker
*Attorney, Agent, or Firm*—Depaoli & O'Brien

[57] ABSTRACT

This invention provides a novel class of diacetylenic monomers and corresponding polydiacetylenic polymers.

Illustrative of the invention is a polymer characterized by the repeating unit:

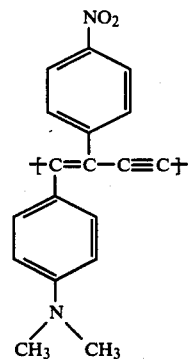

In the form of an optically transparent medium with a noncentrosymmetric alignment of molecules, the polymer exhibits exceptional second order nonlinear optical susceptibility effects.

15 Claims, No Drawings

NOVEL DIACETYLENIC AND POLYDIACETYLENIC COMPOSITIONS

BACKGROUND OF THE INVENTION

The field of nonlinear optics has potential for important applications in optical information processing, telecommunications and integrated optics.

Recently it has been recognized that organic and polymeric materials with large delocalized $\pi$-electron systems can exhibit nonlinear optical response, which in many cases is a much larger response than by inorganic substrates.

In addition, the properties of organic and polymeric materials can be varied to optimize other desirable properties, such as mechanical and thermoxidative stability and high laser damage threshold, with preservation of the electronic interactions responsible for nonlinear optical effects.

Thin films of organic or polymeric materials with large second-order nonlinearities in combination with silicon-based electronic circuitry have potential as systems for laser modulation and deflection, information control in optical circuitry, and the like.

Other novel processes occurring through third-order nonlinearity such as degenerate four-wave mixing, whereby real-time processing of optical fields occurs, have potential utility in such diverse fields as optical communications and integrated circuit fabrication.

Of particular importance for conjugated organic systems is the fact that the origin of the nonlinear effects is the polarization of the $\pi$-electron cloud as opposed to displacement or rearrangement of nuclear coordinates found in inorganic materials.

U.S. Pat. No. 4,431,263 describes nonlinear optical materials based on polymerized diacetylenes. There is a detailed elaboration of physical and theoretical principles which underlie nonlinear behavior in organic systems. Reference is made to Physical Review A, 20 (No. 3), 1179 (1979) by Garito et al, entitled "Origin of the Nonlinear Second-Order Optical Susceptibilities of Organic Systems".

Other U.S. patents which describe the synthesis and properties of diacetylenes and polydiacetylene compositions include U.S. Pat. Nos. 2,855,441; 3,065,283; 3,923,622; 3,994,867; 3,999,946; 4,125,534; 4,195,055; 4,195,058; 4,208,501; 4,215,208; 4,242,440; 4,255,535; 4,328,259; 4,339,951; 4,389,217; 4,439,346; 4,439,514; and prior art cited therein, incorporated herein by reference. British Pat. No. 1,154,191 is of related interest.

Other technical publications which describe diacetylenic properties include Makromol. Chem., 180, 2975 (1979); 182, 965 (1981); 182, 1363 (1981); Mol. Cryst. Liq. Cryst., 93, 239 (1983); 93 247 (1983); 93, 261 (1983); and prior art cited therein, incorporated herein by reference.

Nonlinear optical properties of organic and polymeric materials was the subject of a symposium sponsored by the ACS division of Polymer Chemistry at the 18th meeting of the American Chemical Society, September 1982. Papers presented at the meeting are published in ACS Symposium Series 233, American Chemical Society, Washington, D.C., 1983. Chapters 1 and 8-11 review studies relating to nonlinear optical properties of polydiacetylenes; incorporated herein by reference.

There is continuing research effort to develop new nonlinear optical organic systems for prospective novel phenomena and devices adapted for laser frequency conversion, information control in optical circuitry, light valves and optical switches. The potential utility of organic materials with large second-order and third-order nonlinearities for very high frequency application contrasts with the bandwidth limitations of conventional inorganic electrooptic materials.

Accordingly, it is an object of this invention to provide a novel polymeric composition having an extended conjugated polyunsaturated structure.

It is another object of this invention to provide a thermoplastic polydiacetylenic composition having anisotropic properties.

It is another object of this invention to provide a polydiacetylenic composition which exhibits exceptional nonlinear optical effects.

It is another object of this invention to provide a polymeric nonlinear optical medium which possesses a unique combination of thermoxidative stability and high laser damage threshold.

It is a further object of this invention to provide a novel class of conjugated diacetylenic monomers.

Other objects and advantages of the present invention shall become apparent from the accompanying description and example.

DESCRIPTION OF THE INVENTION

One or more objects of the present invention are accomplished by the provision of a polymeric composition which is characterized by the recurring monomeric unit:

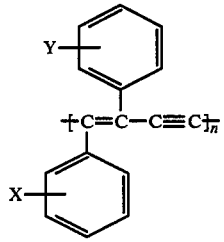

where X is an electron-donating substituent; Y is an electron-withdrawing substituent; and n is an integer of at least 3.

The term "electron-donating" as employed herein refers to organic substituents which contribute x-electrons when the conjugated electronic structure is polarized by the input of electromagnetic energy.

The term "electron-withdrawing" as employed herein refers to electronegative organic substituents which attract $\pi$-electrons when the conjugated electronic structure is polarized by the input of electromagnetic energy.

Illustrative of electron-donating substituents as represented by X in the above formula are amino, alkylamino, dialkylamino, 1-piperidino, 1-piperazino, 1-pyrrolidino, acylamino, hydroxyl, thiolo, alkylthio, arylthio, alkoxy, aryloxy, halo, alkyl, and the like.

Illustrative of electron-withdrawing substituents as represented by Y in the above formula are nitro, cyano, trifluoromethyl, acyl, carboxy, alkanoyloxy, aryloxy, alkoxysulfonyl, aryloxysulfonyl, and the like.

In another embodiment the present invention provides a polyacetylenic composition having anisotropic properties which is characterized by the recurring monomeric unit:

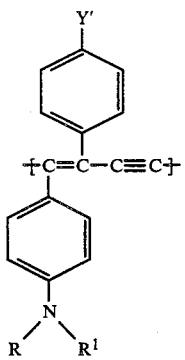

where R and $R^1$ are alkyl groups containing between about 1–20 carbon atoms, and R and $R^1$ taken together with the connecting nitrogen atom form an alicyclic substituent; Y' is a substituent selected from nitro, cyano and trifluoromethyl radicals; and the weight average molecular weight of the polymer is in the range between about 1000–500,000.

Illustrative of alkyl groups are methyl, ethyl, butyl, isobutyl, hexyl, decyl, hexadecyl, eicosyl, and the like.

In another embodiment this invention provides a process for production of a polydiacetylenic composition which comprises polymerizing a diacetylene monomer corresponding to the formula:

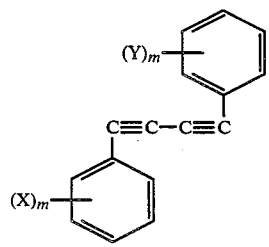

where X is an electron-donating substituent, Y is an electron-withdrawing substituent, and m is the integer one or two.

The polymerization reaction proceeds readily if the acetylene monomer is exposed to ultraviolet radiation, or if the monomer is heated to a temperature sufficiently high for initiation of the polymerization reaction.

In a typical procedure the acetylene monomer is heated to form an anisotropic melt phase and as necessary the temperature is elevated until the polymerization reaction is initiated and completed. The polymerization reaction temperature usually will be in the range between about 200°–275° C. A polymerization catalyst such as a peroxide can be employed if it is desirable to accelerate the rate of polymerization.

A film of the polydiacetylenic composition can be prepared by forming a thin substrate of the diacetylene monomer in a highly ordered state, and then polymerizing the monomer in the substrate to form a corresponding thin polymeric film.

A present invention polydiacetylenic composition can be formed into sheets, films, fibers or other shaped articles by conventional techniques such as extrusion, molding or casting.

The weight average molecular weight of a present invention polyacetylenic composition can be controlled within the range between about 1000–500,000, depending on the reactivity of the diacetylene monomer and the polymerization conditions. In terms of inherent viscosity (I.V.), the preferred polydiacetylenes commonly will exhibit an I.V. of about 2.0–10.0 dl/g when dissolved in a concentration of 0.1 percent by weight in pentafluorophenol at 60° C.

DIACETYLENE MONOMER SYNTHESIS

In another embodiment this invention provides a novel class of conjugated diacetylenic monomers corresponding to the formula:

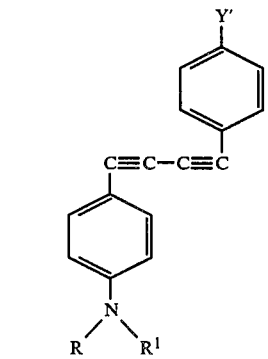

where R and $R^1$ are alkyl groups containing between about 1–20 carbon atoms, and R and $R^1$ taken together with the connecting nitrogen atom form an alicyclic substituent; and Y' is a substituent selected from nitro, cyano and trifluoromethyl radicals.

Illustrative of the novel diacetylene compounds are 1-(4-dimethylaminophenyl)-4-(4-nitropheny)-1,3-butadiyne; 1-(4-dimethylaminophenyl)-4-(4-cyanophenyl)-1,3-butadiyne; 1-(4-dimethylaminophenyl)-4-(4-trifluoromethyl)-1,3-butadiyne; and the like.

The diacetylene monomers utilized for the preparation of the present invention polydiacetylenic compositions can be synthesized by conventional procedures such as the general methods described in references listed in the Background Of The Invention disclosure hereinabove.

The following flow diagram illustrates a reaction scheme for synthesis of a diacetylene compound:

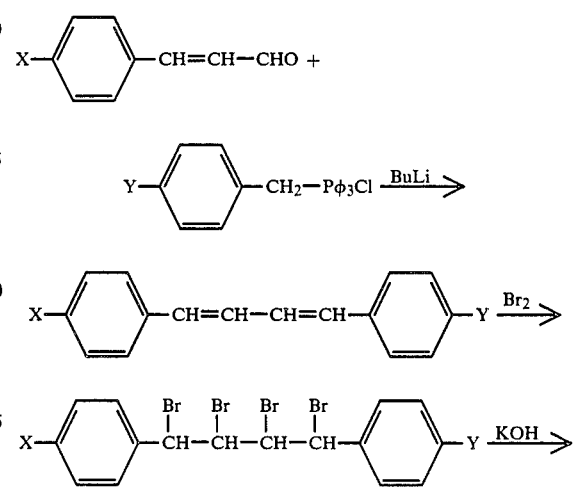

-continued

NONLINEAR OPTICAL PROPERTIES

In another embodiment this invention provides a polydiacetylenic composition having nonlinear optical properties which is characterized by the recurring monomeric unit:

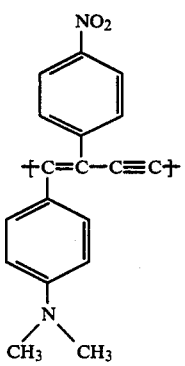

where said polymer has a weight average molecular weight in the range between about 2000–100,000.

In another embodiment this invention provides a polydiacetylenic composition having nonlinear optical properties which is characterized by the recurring monomeric unit:

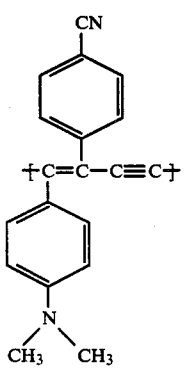

where said polymer has a weight average molecular weight in the range between about 2000–100,000.

In another embodiment this invention provides a polydiacetylenic composition having nonlinear optical properties which is characterized by the recurring monomeric unit:

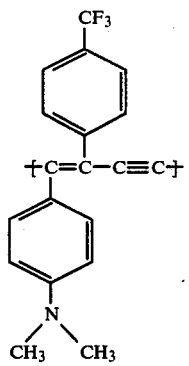

where said polymer has a weight average molecular weight in the range between about 2000–100,000.

The polydiacetylenic compositions illustrated above exhibit a THG $\chi^{(3)}$ susceptibility value greater than about $10 \times 10^{-12}$ esu. The THG $\chi^{(3)}$ response time is less than about $1 \times 10^{-14}$ second.

The fundamental concepts of nonlinear optics and their relationship to chemical structures can be expressed in terms of dipolar approximation with respect to the polarization induced in an atom or molecule by an external field.

As summarized by Twieg and Jain in chapter 3 of ACS Symposium Series 233, the fundamental equation (1) below describes the change in dipole moment between the ground state $\mu_g$ and an excited state $\mu_e$ expressed as a power series of the electric field E which occurs upon interaction of such a field, as in the electric component of electromagnetic radiation, with a single molecule. The coefficient $\alpha$ is the familiar linear polarizability, $\beta$ and Y are the quadratic and cubic hyperpolarizabilities, respectively. The coefficients for these hyperpolarizabilities are tensor quantities and therefore highly symmetry dependent. Odd order coefficients are nonvanishing for all molecules, but the even order coefficients such as $\beta$ (responsible for second harmonic generation, SHG) are zero for centrosymmetric molecules. The odd order coefficient Y is responsible for third harmonic generation (THG).

Equation (2) is identical with (1) except that it describes a macroscopic polarization, such as that arising from an array of molecules in a crystal.

$$\Delta\mu = \mu_e - \mu_g = \alpha E + \beta EE + \gamma EEE + \ldots \quad (1)$$

$$P = P_0 + \chi^{(1)}E + \chi^{(2)}EE + \chi^{(3)}EEE + \ldots \quad (2)$$

Light waves passing through an array of molecules can interact with them to produce new waves. This interaction may be interpreted as resulting from a modulation in refractive index or alternatively as a nonlinearity of the polarization. Such interaction occurs most efficiently when certain phase matching conditions are met, requiring identical propagation speeds of the fundamental wave and harmonic wave. Birefringent crystals often possess propagation directions in which the refractive index for the fundamental $\omega$ and the second harmonic $2\omega$ are identical so that dispersion may be overcome.

A present invention polydiacetylenic medium typically is an optically clear thin film which exhibits hyperpolarization tensor properties such as second harmonic and third harmonic generation, and the linear electrooptic (Pockels) effect. For second harmonic generation, the bulk phase of the polymeric substrate does not possess a real or orientational average inversion center; the substrate is a noncentrosymmetric dipolar structure.

In another embodiment this invention provides a nonlinear optical medium comprising a noncentrosymmetric configuration of aligned molecules of a polymer characterized by the recurring monomeric unit:

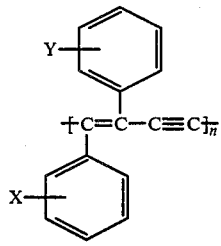

where X is an electron-donating substituent; Y is an electron-withdrawing substituent; and n is an integer of at least 3; and wherein the nonlinear optical medium exhibits a Miller's delta of at least one square meter/coulomb.

For purposes of the present invention, a diacetylenic monomer or polymer is adapted to exhibit the external field-induced macroscopic nonlinearity required for second order harmonic generation.

In another embodiment this invention provides nonlinear optically transparent host polymeric substrates having incorporated therein a distribution of guest diacetylenic monomer, oligomer or polymer molecules.

Illustrative of this type of optical substrate is a polymethyl methacrylate film containing a distribution of polydiacetylenic molecules.

If the distribution of guest molecules is random, there is orientational averaging by statistical alignment of the dipolar molecules in the polymeric host, and the optical substrate exhibits third order nonlinearity ($\chi^{(3)}$).

If the distribution of guest molecules is at least partially uniaxial in molecular orientation, then the optical substrate exhibits second order nonlinearity ($\chi^{(2)}$) One method for preparing polymeric films with large second-order nonlinear coefficients is to remove the orientational averaging of a dopant molecule with large $\beta$ by application of an external DC electric field to a softened film. This can be accomplished heating the film above the host polymer glass-transition temperature $T_g$, then cooling the film below $T_g$ in the presence of the external field. The poling provides the alignment predicted by the Boltzmann distribution law.

The formation of a thin host polymer substrate containing guest molecules having, for example, uniaxial orthogonal molecular orientation can be achieved by inducing a dipolar alignment of the guest molecules in the substrate with an externally applied field of the type described above.

In one method a thin film of the host polymer (e.g., polymethyl methacrylate) containing guest molecules (e.g., polydiacetylenic polymer) is cast between electrode plates. The host polymer substrate then is heated to a temperature above the second order transition temperature of the host polymer. A dc electric field is applied (e.g., at a field strength between about 400–100,000 V/cm) for a period sufficient to align the guest molecules in a unidirectional configuration parallel to the transverse field. Typically the orientation period will be in the range between about one second and one hour, as determined by factors as guest molecular weight and field strength.

When the orientation of guess molecules is complete, the host polymer substrate is cooled below its second order transition temperature, while the substrate is still under the influence of the applied dc electric field. In this manner the uniaxial molecular orientation of guest molecules is immobilized in a rigid structure.

The uniaxial molecular orientation of the guest molecules in the host polymer substrate can be confirmed by X-ray diffraction analysis. Another method of molecular orientation measurement is by optical characterization, such as optical absorption measurements by means of a spectrophotometer with a linear polarization fixture.

Harmonic generation measurements relative to quartz can be performed to establish the value of second order and third order nonlinear susceptibility of the optically clear substrates.

A suitable apparatus for harmonic generation is schematically represented in Macromolecules, 15, 1386 (1982). The apparatus is a Q-switched $Nd^{3+}$/YAG laser configured as an unstable resonator with polarization output coupling. The laser is operated just above threshold, supplying 2–5 per pulse of 1.06 $\mu$m radiation, which is focused on the surface of the thin substrate (20–30 $\mu$m thickness). Variation of the laser polarization is accomplished with a double-quarter wave rhomb rotator. The harmonic light is collected with f/16 optics, filtered from the fundamental light, and passed through a 20-cm focal length grating monochromator with an 8-nm bandwidth. Detection is accomplished with an 11-stage amplified photomultiplier tube. The system is integrated with a computer-controlled gated electronic detection and digitization apparatus. The term "thin substrate" as employed herein refers to a continuous phase solid film, sheet or coating which has a thickness between about 10–500 microns. The term "optically clear" as employed herein refers to a medium which is transparent or light transmitting with respect to incident fundamental light frequencies and harmonic light frequencies. In an electrooptic light modulator device, a present invention nonlinear optical lens medium is transparent to both the incident and exit light frequencies.

The term "Miller's delta" as employed herein with respect to second harmonic generation (SHG) is defined by Garito et al in Chapter 1, "Molecular Optics: Nonlinear Optical Properties Of Organic And Polymeric Crystals"; ACS Symposium Series 233 (1983)

The quantity "delta"($\delta$) is defined by the equation:

$$D_{ijk} = \epsilon_0 \chi_{ii} \chi_{jj} \chi_{kk} \delta_{ijk}$$

where terms such as $\chi_i^{(1)}$ are the linear susceptibility components, and $d_{ijk}$, the second harmonic coefficient, is defined through $$\chi_{ijk}(-2\omega;\omega,\omega) = 2d_{ijk}(-2\omega;\omega,\omega)$$

The Miller's delta ($10^{-2}$ m$^2$/c at 1.06 $\mu$m) of various nonlinear optical crystalline substrates are illustrated by KDP (3.5), LiNbO$_3$ (7.5), GaAs (1.8) and 2-methyl-4-nitroaniline (160).

In another embodiment this invention provides an electrooptic light modulator device with a polymeric nonlinear optical component comprising an optically transparent medium of a polymer characterized by the recurring monomeric unit:

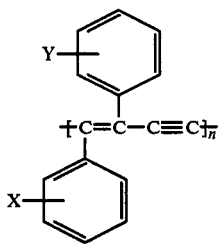

where X is an electron-donating substituent; Y is an electron-withdrawing substituent; and n is an integer of at least 3.

In a further embodiment this invention provides an electrooptic light modulator device with a polymeric nonlinear optical component comprising an optically transparent medium of a polymer characterized by the recurring monomeric unit:

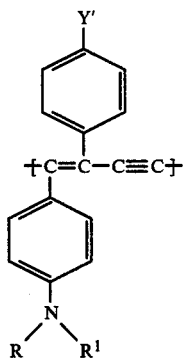

where R and $R^1$ are alkyl groups containing between about 1–4 carbon atoms, and R and $R^1$ when taken together with the connecting nitrogen atom form an alicyclic substituent; Y' is a substituent selected from nitro, cyano and trifluoromethyl radicals; and the weight average molecular weight of the polymer is in the range between about 1000–500,000.

PHYSICAL PROPERTIES

A present invention polydiacetylenic substrate exhibits a unique combination of properties which are adapted for high strength-low weight applications.

A present invention sheet, film or fiber is characterized by a high tensile modulus. It also has excellent thermoxidative stability, and a high laser damage threshold.

The excellent physical properties are attributable mainly to the chemical structure of the polymer molecule chain which consists of an extended resonance-stabilized conjugated unsaturated configuration, and which does not contain any hydrogen atoms in the polymeric backbone.

The following Examples are further illustrative of the present invention. The specific ingredients and processing parameters are presented as being typical, and various modifications can be derived in view of the foregoing disclosure within the scope of the invention.

EXAMPLE

This Example illustrates the preparation and polymerization of 1-(4-dimethylaminophenyl)-4-(4-nitrophenyl)-1,3-butadiyne.

A.

Synthesis Of 4-Nitrophenyltrimethylsilylacetylene

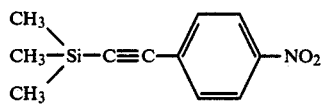

A one liter three-necked flask equipped with a mechanical stirrer, a condenser, and argon inlet and outlet is charged with 33 g (0.163 mole) of 1-bromo-4-nitrobenzene, 0.9 g of dichlorobis(triphenylphosphine)palladium, 180 ml of anhydrous pyridine, 12.0 ml of triethylamine and 25 g (0.255 mole) of trimethylsilylacetylene.

The admixture is reacted at 72° C. for 6 hours, and then the resulting reaction product mixture is poured into an ice-cold solution of 600 ml of hydrochloric acid in 1500 ml of water to precipitate the product from solution. The solid product is recovered by filtration to provide a quantitative yield of 4-nitrophenyltrimethylsilylacetylene, m.p. 95°–100° C. Infrared spectral analysis indicates an absorption peak at 2170 cm$^{-1}$ for the acetylene function.

If 1-bromo-4-cyanobenzene or 1-bromo-4-trifluoromethylbenzene is employed in place of 1-bromo-4-nitrobenzene, then the corresponding 4-cyano or 4-trifluoromethyl substituted product is obtained.

B.

Synthesis Of 4-Nitrophenylacetylene

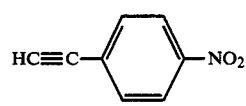

4-Nitrophenyltrimethylsilylacetylene is reacted at ambient temperature for 3 hours with 3 g of potassium carbonate in 300 ml of methanol. The resulting reaction product mixture is poured into 1500 ml of distilled water to precipitate crude 4-nitrophenylacetylene product. The crude product is separated by filtration, washed with water, and dried in a vacuum oven at 50° C. and 1 Torr.

Recrystallization from 3 liters of hexane produces 18.8 g (87.9% overall yield based on 1-bromo-4-nitrobenzene) of pure 4-nitrophenylacetylene, m.p. 150° C. Infrared spectral analysis indicates absorption peaks at 2100 (C≡C) and 3270 (≡CH) cm$^{-1}$.

C.

Synthesis Of 1-Bromo-2-(4-nitrophenyl)acetylene

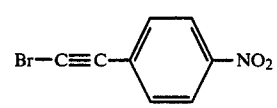

A solution of 5.88 g of 4-nitrophenylacetylene in 50 ml of tetrahydrofuran is added to 10 ml of sodium hypobromite solution, and the admixture solution is stirred at ambient temperature for 16 hours.

A solution of 5 g of ammonium chloride in 15 ml of water is added to the reaction medium to destroy the excess sodium hypobromite. The resulting reaction product mixture is poured into 1500 ml of water to precipitate a crude product. The crude product is separated by filtration, washed with water, to yield 9.1 g of 1-bromo-2-(4-nitrophenyl)acetylene, m.p. 170° C. Infrared spectral analysis indicates an absorption at 2200 cm$^{-1}$ for acetylene (C≡C).

D.

Synthesis Of 1-(4-N,N-dimethylaminophenyl)-4-(4-nitrophenyl)-1,3-butadiyne.

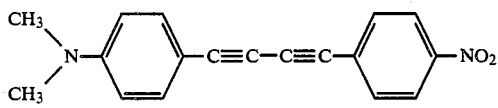

A 300 ml three-necked flask equipped with a mechanical stirrer, an addition funnel, and nitrogen inlet and outlet is charged with 0.747 g of hydroxylamine hydrochloride, 15 ml of butylamine, 15 mg of cuprous chloride and 1.59 g of 4-N,N-dimethylaminophenylacetylene.

A solution of 3.07 g (0.0136 mole) of 1-bromo-4-nitrophenylacetylene in 50 ml of tetrahydrofuran is added dropwise to the admixture in the reactor over a period of 30 minutes at a temperature of 20° C. The reaction mixture is maintained at 38° C. for 1.5 hours, and then poured into ice water to precipitate a crude product. The crude product is separated by filtration, washed with water, and chromatographed on silica gel to yield purified 1-(4-N,N-dimethylaminophenyl)-4-(4-nitrophenyl)-1,3-butadiyne.

If 4-(1-piperazyl)phenylacetylene or 4-butoxyphenylacetylene is employed in place of 4-N,N-dimethylaminophenylacetylene, then the corresponding 4-(1-piperazyl) or 4-butoxy product is obtained.

E.

Preparation Of Polymer

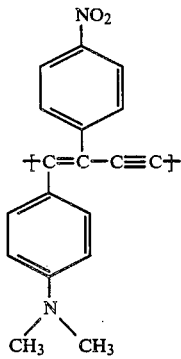

A sample of 1-(4-N,N-dimethylaminophenyl-4-(4-nitrophenyl)-1,3-butadiyne in tetrahydrofuran is cast on an optical glass substrate, and the solvent is evaporated to form a coating on the substrate.

The coated glass substrate is heated at 250° C. for ten minutes to produce a transparent continuous film of polymer on the glass surface.

The transparent polymeric film exhibits a third order nonlinear optical susceptibility $\chi^{(3)}$ value of about $6 \times 10^{-12}$ esu as determined by the method described on page 7 by Garito in "Nonlinear Optical Properties of Organic and Polymeric Materials", ACS Symposium Series 233, American Chemical Society, Washington, D.C. 1983.

If the polymer film is heated above its glass transition temperature while under the influence of a DC electric field, and then cooled below the glass transition temperature while still under the influence of the applied DC electric field (e.g., a field strength between about 1000–50,000 V/cm), a noncentrosymmetric molecular orientation of polymer molecules is achieved.

The film with an external field-induced noncentrosymmetric macroscopic orientation of polymer molecules exhibits second order nonlinear optical susceptibility $\chi^{(2)}$ properties.

A present invention transparent polymeric medium is applicable as a nonlinear optical component in an electrooptic light modulator device.

What is claimed is:

1. A polymeric composition which is characterized by the recurring monomeric unit:

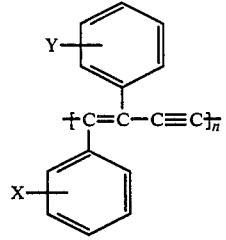

where X is an electron-donating substituent; Y is an electron-withdrawing substituent; and n is an integer of at least 3.

2. A polydiacetylenic composition having anisotropic properties which is characterized by the recurring monomeric unit:

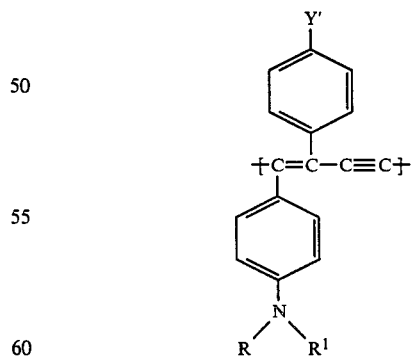

where R and R$^1$ are alkyl groups containing between about 1–20 carbon atoms, and R and R$^1$ taken together with the connecting nitrogen atom form an alicyclic substituent; Y' is a substituent selected from nitro, cyano and trifluoromethyl radicals; and the weight average molecular weight of the polymer is in the range between about 1000–500,000.

3. A polydiacetylenic composition having nonlinear optical properties which is characterized by the recurring monomeric unit:

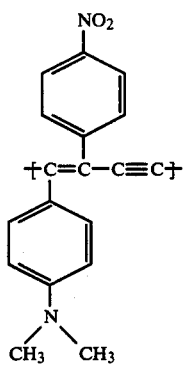

where said polymer has a weight average molecular weight in the range between about 2000–100,000.

4. A polydiacetylenic composition having nonlinear optical properties which is characterized by the recurring monomeric unit:

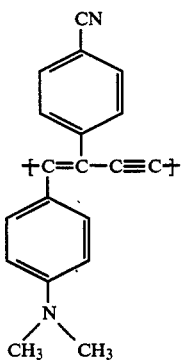

where said polymer has a weight average molecular weight in the range between about 2000–100,000.

5. A polydiacetylenic composition having nonlinear optical properties which is characterized by the recurring monomeric unit:

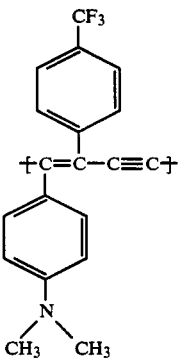

where said polymer has a weight average molecular weight in the range between about 2000–100,000.

6. A process for production of a polydiacetylenic composition which comprises polymerizing a diacetylene monomer corresponding to the formula:

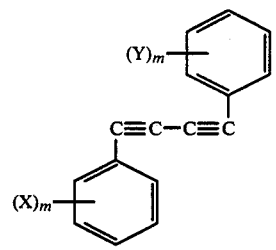

where X is an electron-donating substituent, Y is an electron-withdrawing substituent, and m is the integer one or two.

7. A process in accordance with claim 6 wherein the X substituent is dimethylamino.

8. A process in accordance with claim 6 wherein the Y substituent is nitro.

9. A process in accordance with claim 6 wherein the Y substituent is cyano.

10. A process in accordance with claim 6 wherein the Y substituent is trifluoromethyl.

11. A nonlinear optical medium comprising a noncentrosymmetric configuration of aligned molecules of a polymer characterized by the recurring monomeric unit:

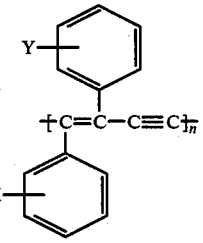

where X is an electron-donating substituent; Y is an electron-withdrawing substituent; and n is an integer of at least 3; and wherein the nonlinear optical medium exhibits a Miller's delta of at least one square meter/coulomb.

12. A nonlinear optical medium in accordance with claim 11 wherein the polymer is polymerized 1-(4-Dimethylaminophenyl)-4-(4-nitrophenyl)-1,3-butadiyne.

13. A nonlinear optical medium in accordance with claim 11 wherein the polymer is polymerized 1-(4-Dimethylaminophenyl)-4-(4-cyanophenyl)-1,3-butadiyne.

14. A nonlinear optical medium in accordance with claim 11 wherein the polymer is polymerized 1-(4-Dimethylaminophenyl)-4-(4-trifluoromethylphenyl)-1,3-butadiyne.

15. A nonlinear optical medium comprising a centrosymmetric configuration of polymeric molecules characterized by the recurring monomeric unit:

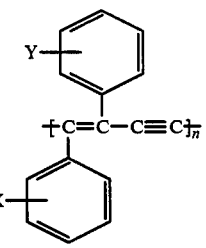

where X is an electron-donating substituent; Y is an electron-withdrawing substituent; and n is an integer of at least 3; and wherein the nonlinear optical medium exhibits a third order optical susceptibility $\chi^{(3)}$ value greater than about $10 \times 10^{-12}$.

* * * * *